United States Patent [19]

Roder et al.

[11] 4,186,052
[45] Jan. 29, 1980

[54] NADH PEROXIDASE FOR HYDROGEN PEROXIDE DETERMINATION

[75] Inventors: Albert Röder, Seeshaupt; Hans Möllering, Tutzing; Wolfgang Gruber, Tutzing-Unterzeismering; Klaus Beaucamp; Hans Seidel, both of Tutzing; Peter Stahl, Bernried; Detlef von Hoerschelmann, Wielenbach, all of Fed. Rep. of Germany

[73] Assignee: Boehringer Mannheim GmbH, Mannheim Waldhof, Fed. Rep. of Germany

[21] Appl. No.: 811,422

[22] Filed: Jun. 29, 1977

[30] Foreign Application Priority Data

Jul. 27, 1976 [DE] Fed. Rep. of Germany ....... 2633728

[51] Int. Cl.$^2$ ..................... C07G 7/02; G01N 31/14; C12D 13/10
[52] U.S. Cl. ...................................... 435/28; 435/192
[58] Field of Search ........... 195/62, 103.5 R, 103.5 C, 195/65, 66 R

[56] References Cited

U.S. PATENT DOCUMENTS 3,886,045  5/1975  Meiattini ...................... 195/103.5 C

OTHER PUBLICATIONS

Dolin, J. Biol. Chem. 225 (1957), pp. 557-573.

Dixon, Enzymes, Academic Press Inc., New York, (1964), pp. 33-39.

*Primary Examiner*—David M. Naff
*Attorney, Agent, or Firm*—Sprung, Felfe, Horn, Lynch & Kramer

[57] ABSTRACT

A novel peroxidase for reduced nicotinamide-adenine-dinucleotide is provided which peroxidase oxidizes reduced nicotinamide-adenine-dinucleotide with hydrogen peroxide to give nicotinamide-adenine-dinucleotide and water and is characterized by a Michaelis constant $K_M$ to hydrogen peroxide of $2.8 \times 10^{-5}$ M and
to reduced nicotinamide-adenine-dinucleotide of $1.7 \times 10^{-5}$ M, measured at 25° C. in 0.2M tris buffer of pH 6.0, containing 0.1M potassium acetate. The peroxidase can be prepared by liberating the enzyme from *Streptococcus faecalis* ATCC 8043 by digestion or by treatment with a surface-active agent and isolating same from the enzyme solution obtained. Hydrogen peroxide is determined in a simple reaction or in a coupled reaction with a specific oxidase by contacting the said peroxidase with the $H_2O_2$ producing reaction mixture at a pH of from 6.0 to 9.0 and measuring the change of extinction as a measure of $H_2O_2$ and of the concentration of nicotinamide-adenine-dinucleotide initially present in said reaction mixture.

9 Claims, 2 Drawing Figures

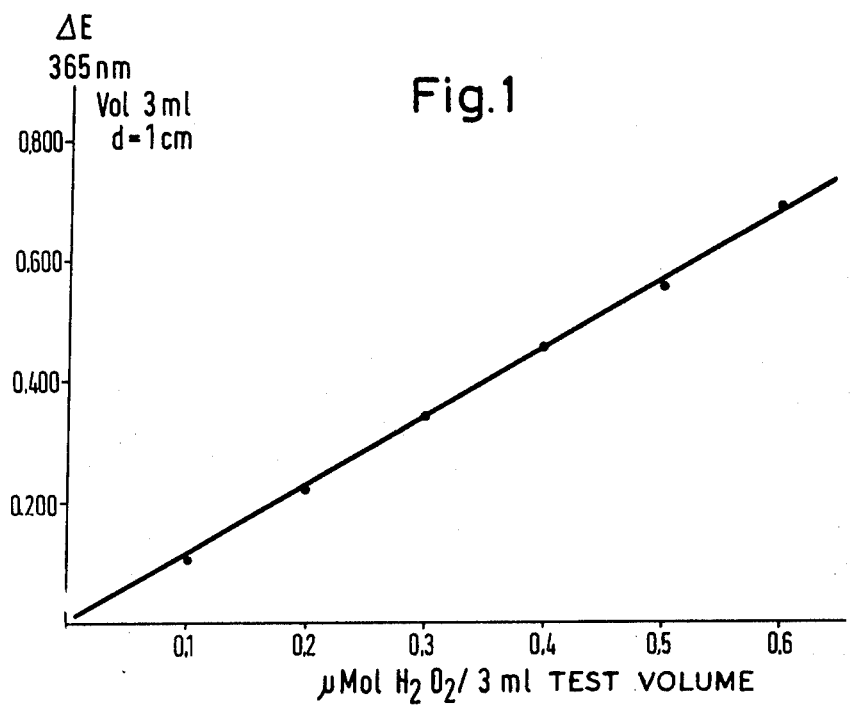
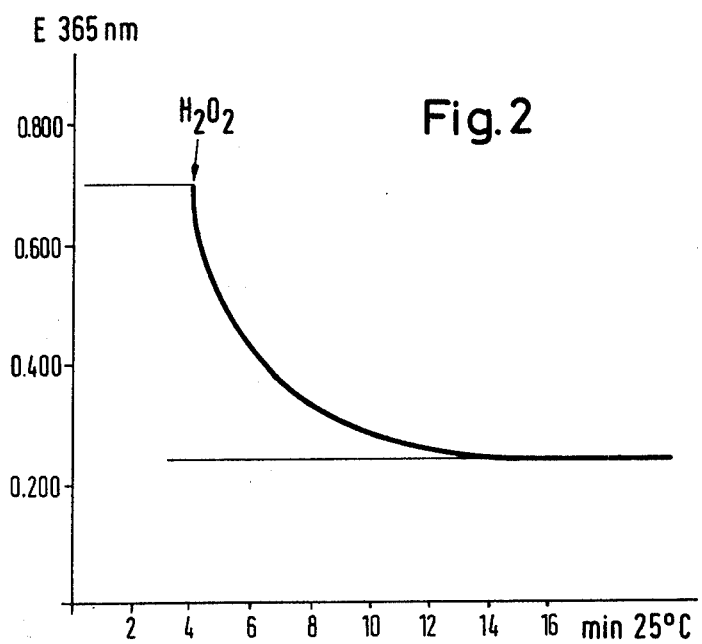

NADH PEROXIDASE FOR HYDROGEN PEROXIDE DETERMINATION

The invention relates to a new composition of matter, to a process for making it, and to a novel diagnostic method utilizing same. More specifically, the present invention is concerned with a new peroxidase for the reduced form of nicotinamide-adenine-dinucleotide (hereinafter referred to as NADH-POD) derived from micro-organisms, which peroxidase differs in various properties from the known NADH-peroxidases and also with a process for its production, as well as the use thereof for the determination of hydrogen peroxide, especially in a coupled reaction in the presence of a specific oxidase.

Numerous important substances, such as glucose, uric acid, cholesterol, amino acids, alcohols and the like can be determined enzymatically with the use of oxidases which, in the course of reaction, form hydrogen peroxide. The hydrogen peroxide formed is subsequently measured by various methods, such as the oxidation of a chromogen and the oxidation of alcohols with catalase (Hantz's reaction), with aldehyde dehydrogenase and the like. However, all these known indicator reactions suffer from certain disadvantages. Thus, the peroxidation of chromogens can be disturbed by certain pharmaceuticals, the detection with the use of Hantz's reaction requires a very long reaction time, the carrying out of the reaction via the aldehyde-dehydrogenase is laborious and the enzyme is very unstable and the like. Therefore, there is a need for a simple detection method for hydrogen peroxide which does not suffer from these disadvantages and can, in particular, also be used in combination with specific oxidases.

It would be highly desirable to be able to couple the specific oxidase reaction leading to the formation of hydrogen peroxide with the NADH reaction, preferably employed for the enzymatic determination (NADH=nicotinamide-adenine-dinucleotide in reduced form). An NADH-POD which catalyzes the reaction

$$NADH + H^+ + H_2O_2 \xrightarrow{NADH\text{-}POD} NAD^+ + 2H_2O$$

is already known (see ABB, 55, 415/1955; and JBC, 225, 557/1957). This enzyme (EC No. 1.11.1.1), which was found in *Streptococcus faecalis* 10 C 1 and in *Lactobacillus casei*, has a pH optimum at 5.4, as well as by Michaelis constants $K_M$ for hydrogen peroxide of $2 \times 10^{-4}$ and for NADH of $1.4 \times 10^{-5}$. Since, for many oxidases, only pH values in the alkaline range are suitable but the known NADH-POD is already practically inactive at pH 7.0 (Arch. Biochem. Biophys. 111, 535/1965) and also has unfavorable Michaelis constants, in practice the known enzyme is not suitable for the determination of hydrogen peroxide in a coupled reaction with a specific oxidase.

We have now found a new NADH-POD which does not suffer from the disadvantages of the known NADH-POD, from which it clearly differs, and which can be used for the enzymatic determination of hydrogen peroxide, especially in a coupled reaction with a specific oxidase.

Thus, according to the present invention, there is provided an NADH-POD which oxidizes NADH with hydrogen peroxide to NAD and water and has a Michaelis constant $K_M$ to hydrogen peroxide of $2.8 \times 10^{-5}$ M and to NADH of $1.7 \times 10^{-5}$ M, measured at 25° C. in 0.2 M tris-(hydroxymethyl)-aminomethane buffer (TRIS buffer) of pH 6.0, containing 0.1 M potassium acetate.

Because of its low $K_M$, the new enzyme is substantially better suited than the known enzyme for the determination of hydrogen peroxide. Thus, the higher is the $K_M$, the higher must be the hydrogen peroxide concentration in the steady state in the case of a determination. However, the higher is the hydrogen peroxide concentration, the greater is also the influence of the catalase which must be, as a rule, present in the sample material. However, due to the competition of the catalase for the hydrogen peroxide, false results are obtained.

Like the known enzyme, the new enzyme of the present invention is a flavoprotein and has, therefore, a yellowish colour. In glycerol/water (1:1 v/v), the enzyme is stable for several months at +4° C. Reduced nicotinamide-adenine-dinucleotide phosphate (NADPH) cannot replace NADH, in contradistinction to the known enzyme which, with NADPH, exhibits about 8% of the reaction velocity referred to that with NADH.

In TRIS buffer in the presence of acetate or propionate ions, the enzyme has a pH optimum at 6.0. The activity in sodium acetate buffer at pH 5.4, i.e. under the optimum conditions of the known enzyme, is about 20% lower. At pH 9.0, the activity is still about 20% of the optimum.

According to the present invention, the new enzyme is obtained from *Streptococcus faecalis* ATCC 8043. Production can take place by digestion or by treatment of the micro-organism with a surface-active agent with the liberation of the enzyme, which can then be isolated. Examples of digestion methods which can be used include the action of ultrasonic waves, trituration with glass pearls, the action of high shear forces and the like. All these methods of digestion are known and conventional for micro-organisms.

Treatment with a surface-active agent preferably takes place at a temperature of from 25° to 60° C. Treatment is preferably carried out at 45° to 55° C. at a pH value of from about 4.5 to 6.0. As a rule, treatment for 15 to 30 minutes suffices but this time can be considerably exceeded without disadvantage. Thus, even in the case of action for 3 hours at 55° C., very good yields are still achieved. Treatment with surface-active agents is preferred since, in this case, less impurities go into solution than in the case of mechanical methods of digestion and, therefore, a purer enzyme is obtained from the start. It is preferable to use non-ionic surface-active agents. Especially preferred surface-active agents include polyethylene glycol esters, for example alkylaryl polyethylene glycol esters, such as "Triton" X-100. An especial advantage of this digestion method is also the fact that the content of disturbing NADH oxidase is especially low.

For the production of the new enzyme, the digest solutions are freed from undissolved materials, for example by centrifuging, and the protein fraction containing the enzyme can be precipitated from the clear supernatant obtained. The precipitation can be carried out by the methods usual in biochemistry, such as salting out, for example with ammonium sulphate, precipitation by organic solvents, such as acetone or methanol, precipitation with polyions, such as polyethylene-imine, and the like. A further purification of the crude enzyme preparation can, for example, be carried out by chromatography on adsorbants, such as carboxymethylcellulose, crosslinked dextran, ion exchangers and the like. Furthermore, we have found that the enzyme can also be freed from accompanying substances by an acid treatment, this acid treatment preferably being carried out at a pH value of from 4.2 to 4.8 for 10 to 25 minutes.

Therefore, a preferred method of purification comprises adjusting the aqueous enzyme solution to pH 4.2 to 4.8, separating off insoluble material and fractionating the enzyme present in the supernatant with polyethylene-imine.

It is to be understood that all steps of the production process are carried out in buffered solution. Especially preferred buffers include phosphate buffer, TRIS buffer and acetate buffer but other conventional buffers, such as glycine buffer, borate buffer and the like, can also be used.

The present invention is also concerned with the use of the new NADH-POD for the determination of hydrogen peroxide in a simple reaction or in a coupled reaction with a specific oxidase, the determination preferably taking place at a pH value of from 6.0 to 9.0. In this way, it is possible to couple the specific oxidase reaction with the measurement of the NADH-NAD reaction. As is known, the latter reaction is especially easy to monitor by determination of the change of extinction, which is proportional to the NADH concentration.

By "specific oxidase," there is understood, within the scope of the present invention, enzymes which react with certain substrates and oxygen with the formation of hydrogen peroxide.

Specific oxidases which can be used according to the present invention include glucose oxidase, D-amino acid oxidase, L-amino acid oxidase, cholesterol oxidase, alcohol oxidase, uricase and xanthine oxidase. Consequently, in a coupled reaction, there can be determined, for example, glucose, D-amino acids, such as D-alanine, L-amino acids, such as L-leucine, cholesterol and cholesterol esters, lower alcohols, uric acid, xanthine and hypoxanthine. In a simple reaction, hydrogen peroxide itself can be determined, i.e. not only as an intermediate product as in the presence of the oxidase system.

The measurement of the NADH-POD of the present invention can also be advantageously carried out by the following test:

2.68 ml. TRIS-potassium acetate buffer (0.2 M TRIS+0.15 M potassium acetate): 2.42 g. TRIS+1.42 g. potassium acetate dissolved in 70 ml. water, adjustment with 2 N acetic acid to pH 6.0, made up to 100 ml. with water.

0.20 ml. NADH (6 mM): 5 mg. NADH dissolved with 1 ml. water.

0.02 ml. sample NADH-POD.

Mix, at 365 nm, d=1 cm., 25° C. pre-running ΔE/min. This pre-running (extinction decrease) serves for the calculation of the "NADH-oxidase." Start with 0.10 ml. hydrogen peroxide (40 mM (0.05 ml. 30% hydrogen peroxide are diluted with 10 ml. water))

Mix, measure extinction change/min. (ΔE/min.).

Before calculation of the NADH-POD activity, from ΔE/min. the NADH-oxidase pre-running is subtracted.

TRIS-acetate buffer is preferably employed but the use of NADH-POD is not limited to this buffer system. The determination of hydrogen peroxide with NADH-POD can be carried out, inter alia, with: sodium acetate, piperazine, potassium phosphate, potassium diphosphate, borate/citrate, glycyl-glycine, triethanolamine hydrochloride or HEPES (N-2-hydroxyethylpiperazine-N-ethanesulphonic acid) as buffer system.

In a corresponding manner, the hydrogen peroxide determination can also be carried out by adding NADH-POD in excess and the amount of hydrogen peroxide is determined, which corresponds to the change of extinction. The measurement can be carried out by the end point method or kinetically, i.e. by measurement of the extinction difference within a definite short period of time. The accompanying drawings show the precision and chronological course of the hydrogen peroxide determination at pH 8.0 in the above-described TRIS-potassium acetate buffer and under the above-mentioned measurement conditions.

The utility of the new enzyme according to the present invention for the quantitative determination of hydrogen peroxide is illustrated in the accompanying drawings wherein:

FIG. 1 is a calibration curve in which the amount of hydrogen peroxide (abscissa) is plotted against the extinction difference (ordinate);

FIG. 2 shows the decrease of extinction with the time at 25° C. At the start, 0.4 μMol hydrogen peroxide were added.

The following Examples are given for the purpose of further exemplifying the present invention:

EXAMPLE 1

Production and purification of the new enzyme

*Streptococcus faecalis* ATCC 8043 biomass was heated with a 1% solution of "TRITON" X 100 in 0.02 M potassium phosphate buffer (pH 5.0) for 30 minutes at 55° C. After cooling to 4° C., insoluble material was separated off. An aqueous solution was obtained with an activity of 1.77 U/ml. and a specific activity of 0.77 U/mg.

Ammonium sulphate was added to the solution obtained until all of the enzyme activity was present in the precipitate. The precipitate was filtered off, taken up with phosphate buffer (pH 5.0) and desalted by passage through a molecular sieve. The enzyme solution thus obtained was used for the hydrogen peroxide test directly or after previous concentration by lyophilisation and taking up in 3.0 M ammonium sulphate solution (pH about 7).

Further purification of the starting solution was carried out, without previous separation of the enzyme, by ammonium sulphate precipitation as follows:

The solution was adjusted with acetic acid to pH 4.4 and left to stand for 20 minutes. Insoluble material was then filtered off. Polyethylene-imine solution was added portionwise to the supernatant, insoluble material being filtered off after each addition. The fraction containing the enzyme was again dissolved in a buffer and chromatographed over diethylaminoethylcellulose. Subsequently, desalting was carried out with cross-linked dextran. A preparation was thus obtained with an activity of about 45 U/mg.

EXAMPLE 2

Dependence of the activity of the new NADH-POD upon the buffer employed in the test Measurement was carried out in 0.1 M buffer (1 mM hydrogen peroxide, 0.4 mM NADH).

TABLE 1

Enzyme activites at pH 7.5 in % in various buffers, referred to the activity in sodium acetate buffer (100%)

| buffer | % |
|---|---|
| sodium acetate | 100 |
| TRIS acetate | 101 |
| triethanolamine acetate | 100 |
| piperazine hydrochloride | 100 |
| HEPES | 89 |
| potassium phosphate | 63 |
| potassium diphosphate | 61 |
| borate/citrate | 25 |

EXAMPLE 3

Influence of the pH value in the test system upon the activity of the new NADH-POD Measurement was carried out in 0.1 M TRIS acetate buffer (1 mM hydrogen peroxide, 0.4 mM NADH).

TABLE 2 pH Dependence of the enzyme activity in %

| pH | % |
|---|---|
| 5.0 | 67 |
| 5.4 | 98 |
| 6.0 | 100 |
| 7.0 | 88 |
| 7.5 | 56 |
| 8.0 | 37 |
| 9.0 | 19 |

EXAMPLE 4

Uric acid determination with uricase

The determination was carried out according to the following equation:

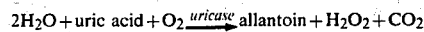

$$2H_2O + \text{uric acid} + O_2 \xrightarrow{\text{uricase}} \text{allantoin} + H_2O_2 + CO_2$$

Uricase, the new NADH-POD according to the present invention and NADH were dissolved in 0.2 M TRIS acetate buffers of varying pH value, each of which contained 0.15 M potassium acetate. An aqueous solution containing 0.2 μMol uric acid was then added for starting. The following results were obtained:

TABLE 3

| pH | amount of enzyme in test NADH-POD | amount of enzyme in test uricase | end expiry time in min. | % verification, referred to UV test = 100% |
|---|---|---|---|---|
| | U | U | | |
| 6 | 0.1 | 1 | 16 | 95.5 |
| 7 | 0.1 | 1 | 10 | 99 |
| 8 | 0.1 | 1 | 5 | 100 |
| 9 | 0.1 | 1 | 16 | 96.5 |
| 9 | 0.1 | 2 | 10 | 96.5 |
| 10 | 0.2 | 0.2 | 10 | 98 |

Reference method: P. Scheibe, E. Bernt and H. U. Bergmeyer in H. U. Bergmeyer, Methoden der enzymatischen Analyse, Vol. II, 3rd ed., p. 1999 (1974).

| pH | % |
|---|---|
| 6.0 | 71 |
| 7.0 | 95 |
| 8.0 | 100 |
| 8.5 | 98 |
| 9.0 | 76 |
| 10.0 | 69 |

EXAMPLE 5

Glucose determination with glucose oxidase (GOD)

The determination was carried out according to the following equation:

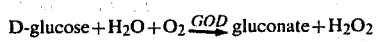

$$\text{D-glucose} + H_2O + O_2 \xrightarrow{GOD} \text{gluconate} + H_2O_2$$

The determination was carried out at pH 7.0, with the use of 210 U GOD, 0.2 U NADH-POD and 60 U mutarotase. The determination of glucose in urine gave 100% of the value obtained by the reference method GOD-peride R (see German Pat. Specification No. 1,648,840 and H. U. Bergmeyer, Methoden der enzymatischen Analyse, Vol. II, 3rd ed., p. 1257 (1974)).

EXAMPLE 6

Determination of D-alanine with D-aminoacid oxidase (D-AOD)

The determination was carried out according to the following equation:

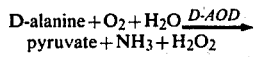

$$\text{D-alanine} + O_2 + H_2O \xrightarrow{D\text{-}AOD} \text{pyruvate} + NH_3 + H_2O_2$$

The determination was carried out at pH 8.5 with the use of 0.25 U NADH-POD, 20 U D-AOD and 5 U lactate dehydrogenase at 25° C. In the case of 20 minutes incubation at 25° C., the verification was 100%. Reference method: M. Grassl in H. U. Bergmeyer, Methoden der enzymatischen Analyse, Vol. II, 3rd ed., p. 1731 (1974).

EXAMPLE 7

Determination of L-leucine with L-amino acid oxidase (L-AOD) from *Crotalus terrificus*

The determination was carried out according to the following equation:

$$\text{L-leucine} + O_2 \xrightarrow{L\text{-}AOD} \text{ketoisocapronic acid} + H_2O_2$$

The determination took place at pH values between 7.5 and 8.0 in 0.2 M TRIS acetate buffer which contained 0.15 M acetate. In the case of the addition of 0.2 U NADH-POD according to the present invention and 0.7 U L-AOD in the test, the verification was about 100%. At a concentration of 0.2 μMol L-leucine, the reaction period was about 20 minutes. Reference method: not known.

EXAMPLE 8

Cholesterol ester determination with cholesterol oxidase and cholesterol esterase The determination was carried out according to the following equations:

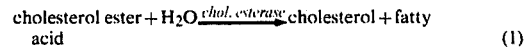

$$\text{cholesterol ester} + H_2O \xrightarrow{\text{chol. esterase}} \text{cholesterol} + \text{fatty acid} \quad (1)$$

$$\text{cholesterol} + O_2 \xrightarrow{\text{chol. oxid.}} \text{cholestenone} + H_2O_2 \quad (2)$$

Use was made of commercially available cholesterol standard solutions and serum. The verification in the case of a commercially available standard solution with 0.2 μMol cholesterol was 98 to 102% at pH values of from 6.0 to 9.0 within the course of 9 to 12 minutes, using 0.1 U NADH-POD and 2 U cholesterol oxidase in 3 ml. test volume.

The cholesterol determination in serum with saponification of esterified cholesterol with ethanolic potassium hydroxide gave verification values of from 95 to 105%. Reference method: P. Ronschlau, E. Bernt and W. Gruber in H. U. Bergmeyer, Methoden der enzymatischen Analyse, Vol. II, 3rd ed., p. 1938 (1974).

EXAMPLE 9

Determination of alcohols with methanol oxidase (MOD)

The determination was carried out according to the following equation:

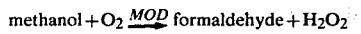

methanol + $O_2$ $\xrightarrow{MOD}$ formaldehyde + $H_2O_2$

The determination was carried out at a pH value of from 9.0 to 9.5 in glycine-sodium pyrophosphate buffer, with the addition of semicarbazide. The amounts of enzyme employed were 0.3 U NADH-POD and 8 U MOD. The verification in the case of 0.2 μMol methanol and ethanol was 100%. The determination can also be carried out with isopropanol.

EXAMPLE 10

Determination of xanthine and hypoxanthine with xanthine oxidase (XOD)

The determination was carried out according to the following equations:

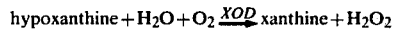

hypoxanthine + $H_2O$ + $O_2$ $\xrightarrow{XOD}$ xanthine + $H_2O_2$

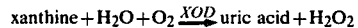

xanthine + $H_2O$ + $O_2$ $\xrightarrow{XOD}$ uric acid + $H_2O_2$

The determination was carried out at pH 8.0 in TRIS buffer as in the preceding Examples. The verification was 100% for xanthine and hypoxanthine. As reference method, there was used the method described in Bergmeyer, "Methoden der enzymatischen Analyse," 3rd ed., Vol. II, p. 1988 (1974).

It will be understood that the specification and examples are illustrative but not limitative of the present invention and that other embodiments within the spirit and scope of the invention will suggest themselves to those skilled in the art.

What is claimed is:

1. Process for the production of peroxidase for reduced nicotinamide-adenine-dinucleotide comprising liberating the enzyme from *Streptococcus faecalis* ATCC 8043 by digestion or by treatment with a surface-active agent and isolating said peroxidase from the enzyme solution obtained, said isolated peroxidase being characterized by a Michaelis constant $K_m$
   to hydrogen peroxide of $2.8 \times 10^{-5}$ M and to reduced nicotinamide-adenine-dinucleotide of $1.7 \times 10^{-5}$ M.
measured at 25° C. in 0.2 M tris buffer of pH 6.0, containing 0.1 M potassium acetate.

2. Process as claimed in claim 1 wherein treatment with a surface-active agent is utilized and is carried out at a temperature of from 25° to 60° C.

3. Process as claimed in claim 2 wherein the treatment with a surface-active agent is carried out at a temperature of from 45° to 55° C. at a pH value of from 4.5 to 6.0.

4. Process as claimed in claim 1 wherein the enzyme solution obtained is adjusted to a pH value of 4.2 to 4.8, insoluble material is separated off and the enzyme present in the supernatant is fractionated with polyethyleneimine.

5. Process as claimed in claim 1 wherein the enzyme is liberated by digestion.

6. Peroxidase for reduced nicotinamide-adenine-dinucleotide, which peroxidase oxidizes reduced nicotinamide-adenine-dinucleotide with hydrogen peroxide to give nicotinamide-adenine-dinucleotide and water and is characterized by a Michaelis constant $K_M$
   to hydrogen peroxide of $2.8 \times 10^{-5}$ M and to reduced nicotinamide-adenine-dinucleotide of $1.7 \times 10^{-5}$ M,
measured at 25° C. in 0.2 M tris buffer of pH 6.0, containing 0.1 M potassium acetate, which peroxidase is produced by the process claimed in claim 1.

7. Method for the determination of hydrogen peroxide which method comprises contacting peroxidase as claimed in claim 6 with an $H_2O_2$ producing reaction mixture containing NADH at a pH of from 6.0 to 9.0 and measuring the change of extinction as a measure of the $H_2O_2$ present.

8. Method for the determination of hydrogen peroxide which comprises contacting peroxidase as claimed in claim 6 with an $H_2O_2$ producing reaction mixture containing NADH and measuring the change of extinction as a measure of the $H_2O_2$ present and of the concentration of reduced nicotinamide-adenine-dinucleotide initially present in said reaction mixture.

9. Process as claimed in claim 8 wherein the specific oxidase used is glucose oxidase, D-amino acid oxidase, L-amino acid oxidase, cholesterol oxidase, alcohol oxidase, uricase or xanthine oxidase.

* * * * *